(12) United States Patent
Munn

(10) Patent No.: US 11,788,265 B2
(45) Date of Patent: Oct. 17, 2023

(54) INTERCHANGEABLE DRAIN DISINFECTING DEVICE WITH UV SOURCE IRRADIATION OPTIMIZATION

(71) Applicant: STERILUMEN, INC., Tarrytown, NY (US)

(72) Inventor: Max Munn, Tarrytown, NY (US)

(73) Assignee: STERILUMEN, INC., Tarrytown, NY (US)

( * ) Notice: Subject to any disclaimer, the term of this patent is extended or adjusted under 35 U.S.C. 154(b) by 0 days.

(21) Appl. No.: 17/199,116

(22) Filed: Mar. 11, 2021

(65) Prior Publication Data
US 2021/0198879 A1    Jul. 1, 2021

Related U.S. Application Data

(63) Continuation-in-part of application No. 16/987,837, filed on Aug. 7, 2020, which is a continuation of
(Continued)

(51) Int. Cl.
| | | |
|---|---|---|
| *E03C 1/126* | (2006.01) | |
| *A61L 2/24* | (2006.01) | |
| *A61L 2/10* | (2006.01) | |

(52) U.S. Cl.
CPC ............. *E03C 1/126* (2013.01); *A61L 2/10* (2013.01); *A61L 2/24* (2013.01); *A61L 2202/11* (2013.01); *A61L 2202/14* (2013.01)

(58) Field of Classification Search
CPC ... E03C 1/126; A61L 2/24; A61L 2/10; A61L 2202/11; A61L 2202/14; F03C 1/126
See application file for complete search history.

(56) References Cited

U.S. PATENT DOCUMENTS

| 3,953,059 A | 4/1976 | Carroll et al. |
|---|---|---|
| 5,225,083 A | 7/1993 | Pappas et al. |

(Continued)

FOREIGN PATENT DOCUMENTS

| CN | 109811837 A | 5/2019 |
|---|---|---|
| JP | 2001095699 A | 4/2001 |

(Continued)

OTHER PUBLICATIONS

"Snell's Law" retrieved from https://personal.math.ubc.ca/~cass/courses/m309-01a/chu/Fundamentals/snell.htm on Oct. 24, 2022. (Year: 2022).*

(Continued)

*Primary Examiner* — David E Smith
(74) *Attorney, Agent, or Firm* — Nolte Lackenbach Siegel; Myron Greenspan

(57) ABSTRACT

A device for disinfecting the interior of a drain pipe having a tubular wall formed with a hole between the sink drain inlet and the U-shaped trap. A UV-C LED module is positioned to register with the hole and includes a UV-C LED that generates a radiation beam having a predetermined radiation angle to transmit UV-C light into the drain pipe through the hole to irradiate at least a portion of said interior surface and expose airborne pathogens contained therein to UV-C light. A lens generally coextensive with the tubular wall has a peripheral edge aligned with the hole. The UV-C LED is spaced from the lens a distance to cause the radiation beam to extend up to but not beyond the peripheral edge of the lens to maximize transmission of UV-C light through the lens to maximize exposure of the interior surface and airborne pathogens to the UV-C light.

9 Claims, 5 Drawing Sheets

Related U.S. Application Data application No. 16/538,296, filed on Aug. 12, 2019, now Pat. No. 10,738,446.

(56) References Cited

U.S. PATENT DOCUMENTS

| | | | |
|---|---|---|---|
| 6,666,966 B1* | 12/2003 | Schluttig | E03C 1/126 |
| | | | 4/677 |
| 6,838,400 B1 | 1/2005 | Japp et al. | |
| 9,750,225 B1 | 9/2017 | Makins | |
| 10,550,011 B2* | 2/2020 | Jung | A61L 2/10 |
| 10,738,446 B1 | 8/2020 | Munn | |
| 2005/0135979 A1 | 6/2005 | Gootter | |
| 2008/0212319 A1* | 9/2008 | Klipstein | B60Q 3/35 |
| | | | 362/231 |
| 2008/0213128 A1* | 9/2008 | Rudy | A61L 2/10 |
| | | | 422/186.3 |
| 2010/0237254 A1 | 9/2010 | Mason et al. | |
| 2011/0008205 A1 | 1/2011 | Mangiardi | |
| 2013/0146783 A1 | 6/2013 | Boodaghians et al. | |
| 2013/0206187 A1 | 8/2013 | Dombrowski | |
| 2013/0233511 A1 | 9/2013 | Swedberg et al. | |
| 2013/0236353 A1 | 9/2013 | Bleschschmidt | |
| 2014/0353519 A1* | 12/2014 | Wang | A01K 63/04 |
| | | | 250/435 |
| 2016/0052802 A1* | 2/2016 | Ochi | C02F 1/325 |
| | | | 250/435 |
| 2016/0271280 A1 | 9/2016 | Liao et al. | |
| 2017/0314243 A1* | 11/2017 | Koll | E03F 5/0407 |
| 2018/0291602 A1* | 10/2018 | Schluttig | E03C 1/28 |
| 2019/0142981 A1 | 5/2019 | Kim et al. | |
| 2019/0214244 A1 | 7/2019 | Park | |
| 2019/0240361 A1 | 8/2019 | Niizeki | |
| 2020/0331775 A1* | 10/2020 | Schowalter | A61L 2/10 |

FOREIGN PATENT DOCUMENTS

| | | |
|---|---|---|
| JP | 2001112855 A | 4/2001 |
| JP | 2010275840 | 12/2010 |
| JP | 2010275841 | 12/2010 |
| JP | 2013185308 | 9/2013 |
| KR | 970101 B1 | 7/2010 |
| KR | 101410192 | 6/2014 |
| KR | 101784210 | 10/2016 |
| KR | 20180002069 | 1/2018 |
| KR | 1835481 B1 | 3/2018 |
| KR | 20180096040 | 8/2018 |
| KR | 101905518 | 10/2018 |
| WO | 2002081829 A1 | 10/2002 |
| WO | 2011032543 A3 | 3/2011 |
| WO | 2019043062 A1 | 3/2019 |

OTHER PUBLICATIONS

"Microbial Characterization of Biofilms in Domestic Drains and the Establishment of Stable BioFilm Microcosms" McBain et al, Applied and Environmental Microbiology, Jan. 2003, 69(1): 177-185.

* cited by examiner

INTERCHANGEABLE DRAIN DISINFECTING DEVICE WITH UV SOURCE IRRADIATION OPTIMIZATION

CROSS-REFERENCE TO RELATED APPLICATIONS

This application is a Continuation-in-Part (CIP) of U.S. patent application Ser. No. 16/987,837 filed on Aug. 7, 2020, currently pending, which was a Continuation of U.S. patent application Ser. No. 16/538,296, filed Aug. 12, 2019 for a DRAIN DISINFECTING DEVICE AND METHOD OF INSTALLING THE SAME.

BACKGROUND OF THE INVENTION

1. Field of the Invention

This invention generally relates to controlling levels of pathogens in sink installations and, more specifically, to an interchangeable drain disinfecting device with UV source irradiation optimization.

2. Description of the Background Art

High levels of moisture in a sink drain pipe create perfect conditions for numerous bacteria and other pathogens to grow and thrive. Also, because organic products and other nutrients are frequently disposed of in hospital sinks and kitchen sinks the drain pipes for these sinks contain extensive levels of bacteria. Disposing hair, soap and dead skin down the sink doesn't just cause blockages, but can also provide the environment for a deadly threat.

Drain pipes between the sink basin and the P-trap or U-trap are ideal for pathogen growth. The inside surfaces of such drain pipes are typically warm, moist and contain nutrients that pathogens can feed on, enabling them to thrive. Bacteria that are health hazard include salmonella that can be fatal with those with compromised immune systems and *E. coli* that can be life-threatening but usually only results in diarrhea, *Fusarium solani* that can lead to permanent vision damage and many more pathogens that can cause urinary tract infections and other illnesses.

When unattended, micro-organisms including virus, bacteria, fungi, diatoms and algae stick together and form biofilms. Micro-organisms like to grow on moist, nutrient-rich surfaces, especially in the presence of bathroom blockages caused by hair, soap, sulfates and oils. Once fully formed, biofilms are notoriously difficult to get rid of as they become immune to antibiotics contained in cleaning agents. In hospitals, where liquids or fluids are commonly poured into hospital sinks, such as unused intravenous fluids and left over beverages, pathogens flourish when they multiply to create biofilms. A film can rise up along the inner surface of a pipe at a rate of 2.5 cm (approximately 1") per day to contaminate sink drain covers. Once a biofilm reaches a sink strainer or inlet it can instantly be spread from the strainer to the countertop surrounding the sink, from where it could be potentially distributed further, either by individuals touching the surface or objects placed upon it. At that point, even clean faucet water can splatter the bacteria and other pathogens around the sink bowl and countertop. With only one sink contaminated, running water even with no nutrients, may be enough for the bacteria to infiltrate other sinks through a common drain pipe and an interconnected plumbing system in just one week.

The micro-organisms that grow inside drain pipes can be varied and dangerous to people when exposed to them, and particularly to those individuals that have lowered or weakened immune systems. Some people only need to be exposed to as little 1 mg or less of *Staphylococcus aureus* to lead to staff-related illness and infection. See, for example, "Microbial Characterization of Biofilms in Domestic Drains and the Establishment of Stable BioFilm Microcosms" McBain et al, Applied and Environmental Microbiology, January 2003, 69(1): 177-185.

A number of solutions have been proposed to control the growth of micro-organisms in drain pipes. In Korean Publication KR2016/6083569A a sterilizing and deodorizing apparatus is disclosed that uses a series of UV LEDS arranged along the inside surface of the actual drain pipe and enclosed within a cylindrical quartz protective cover projecting into the drain pipe, thereby narrowing the drain pipe passageway. The sterilizing and deodorizing apparatus is an OEM product and not suitable for after market installations into existing sinks. In Japanese Publication JP05291487B2 UV LEDS are incorporated within a drainage portion of the sink. The UV LEDs are mounted directly within the drainage portion. The installation provides a hygienic equipment chamber, and is also suitable for OEM installations. Therefore, this device is, likewise, not suitable for use with existing sink fixtures. Another OEM-style product is disclosed in Korean Publication KR2017/0022190A for a sink with ultra-violet ray sterilization function. The disclosed device includes a cover panel as part of a kitchen appliance. The cover panel is transparent and a source of UV is placed below the panel so that kitchen tools, dish towels, kitchen utensils and the like can be placed on top of the cover panel to expose them to the ultra-violet lamp. Japanese Publication JP5945135B2 discloses a drainage part of a sink. A coating layer of a photo-catalyst is applied to the inner surface of the drain cylinder. An LED light source is positioned at the inlet to the drain pipe for transmitting UV through a transparent wall to which an externally positioned LED light source is attached, introducing UV radiation upstream of the drain pipe to promote the decomposition and removal of dirt stuck to the inner surface of the drain cylinder.

The aforementioned devices, as indicated, are primarily for OEM installations or special purpose sink basins, focusing on one region of the sink basin or proximate portion of a drain pipe and do not address the buildup of pathogens along the downstream ends of drain pipes leading up to the traps where micro-organisms can and normally do flourish.

SUMMARY OF THE INVENTION

Accordingly, it is an object of the present invention to provide a drain disinfecting device that does not have the disadvantages of prior art devices.

It is another object of the invention to provide a drain disinfecting device that is easily installed with any new or existing sink drain pipe installation.

It is still another object of the invention to provide a drain disinfecting device as in the previous objects that is simple in construction and economical to manufacture.

It is yet another object of the invention to provide a drain disinfecting device that can be configured and flexibly positioned along a drain pipe to expose most or all of the internal surfaces of drain pipes.

It is a further object of the invention to provide a drain disinfecting device that is effective in eliminating most pathogens that normally proliferate in drain pipes.

It is still a further object of the invention to provide a method for easily, quickly and inexpensively installing a drain disinfecting device in accordance with the invention without the need for specialized sink basins or specialized tools.

It is yet a further object to provide a drain disinfecting device and method of installing the same that enables two or more such devices to be installed along the length of a drain pipe to enhance or maximize elimination of pathogens along all or substantial position of the drain pipe.

The above objects, and others that will become apparent hereinafter, are obtained with a drain disinfecting device in accordance with the invention for disinfecting the interior of a drain pipe leading from a drain inlet of a sink basin to a U-shaped trap beneath the sink basin includes a drain pipe section below or downstream of the sink drain inlet. The drain pipe section has a tubular wall defining an interior space and interior surface and formed with a hole between the sink drain inlet and the U-shaped trap. At least one UV-C LED module is positioned to register with the hole and includes a UV-C LED that when energized generates a radiation beam having a predetermined radiation angle to transmit UV-C light into the drain pipe section through the hole to irradiate at least a portion of the interior surface and expose airborne pathogens contained therein to UV-C light in proximity to the drain inlet. A lens is generally coextensive with the tubular wall and has a peripheral edge aligned with the hole. Energizing means is provided for energizing the at least one UV-C LED module, the UV-C LED being spaced from the lens a predetermined distance to cause the radiation beam to extend up to but not beyond the peripheral edge of the lens to maximize transmission of UV-C light through the lens and maximize exposure of the interior surface to the UV-C light so that energizing the at least one UV-C LED module maximizes exposure of pathogens on the interior surface and airborne pathogens within the interior space to UV-C radiation and reduces the ability of pathogens from entry into the sink basin.

A feature of the invention is that the lens is spaced from said UV-C LED a predetermined distance "s" and has a thickness "t", and the radiation angle is "θ" and the lens has a diameter "D" wherein s=D/[2 tan (θ/2)]−t. Another feature of the invention is that the UV-C LED module is removably attachable to the drain pipe section for replacement or maintenance, sealing means providing a seal against the flow of fluid from the drain pipe section while maintaining the predetermined distance when the UV-C LED module is in a normal fully operative position.

BRIEF DESCRIPTION OF THE DRAWINGS

Those skilled in the art will appreciate the improvements and advantages that derive from the present invention upon reading the following detailed description, claims, and drawings, in which:

DETAILED DESCRIPTION

Figure 1:
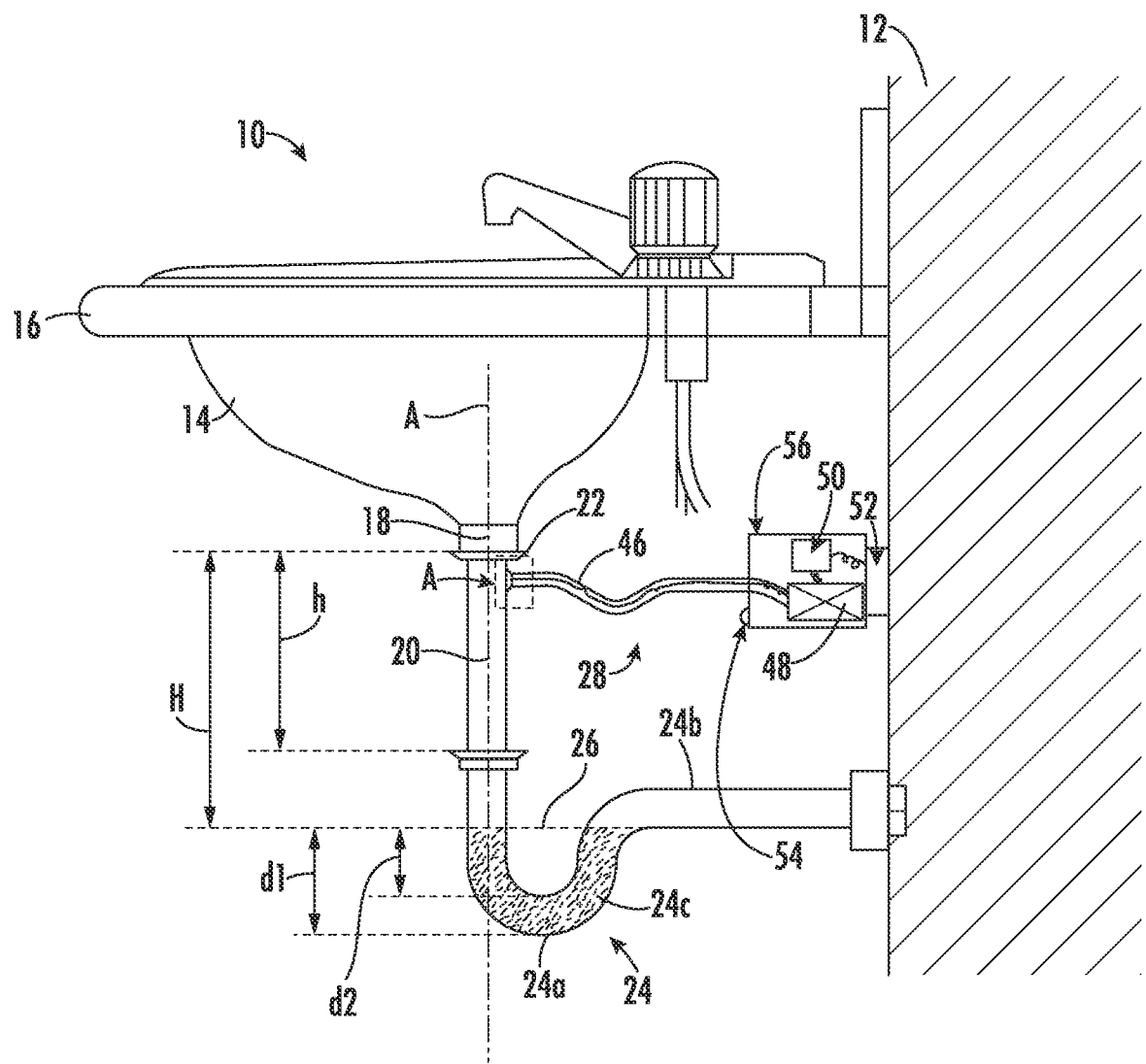
FIG. 1 is a diagrammatic representation of a sink installation, showing how a drain disinfecting device in accordance with the invention can be installed to disinfect the internal surface and pathogen-laden air within a drain pipe.

Referring now specifically to the Figures, in which the identical or similar parts are designated by the same reference numerals throughout, and first referring to FIG. 1, a sink installation is generally designated by the reference numeral 10.

The sink installation 10 can represent a sink, for example, in a bathroom or in a kitchen or elsewhere. As shown, the sink installation is typically mounted on a wall 12, with the sink basin 14 supported on a countertop or support panel 16 and, as with most sink basins, is provided with a fixture tail piece 18 designed to be connected to a drain pipe.

While many different drain pipe configurations are used in connection with different sinks, a simple arrangement is illustrated in FIG. 1 in which the tail piece 18 is joined to a drain pipe 20 by means of a union or a locknut 22. The drain pipe 20 defines a generally vertical axis A. The drain pipe 20, in turn, is connected to an outlet pipe 24 by means of another union or locknut 22 as shown. The outlet pipe 24, sometimes referred as a P-pipe or tube, includes a U-shaped trap 24a and a horizontal extension portion 24b through which waste water is drained to a sewer pipe. Under normal conditions, without blockages, air locks or other pressure differentials, U shaped traps are filled with waste water 24c to a level determined by the overflow level 26. When water rises above the overflow level 26 it flows out through the horizontal extension 24b to the main waste pipes. The regions of the drain pipes that are normally problematic in terms of organism proliferation are designated by the height "H". This region, as suggested, is exposed to moisture, air or oxygen as well as nutrients that are flushed down the drain. The level of the liquid "d1" within the U-shaped trap 24a prevents gases from the sewer pipes entering the space where the sink installation is located through the sink basin. The level "d2" is normally referred to as the trap seal depth and can range between 1.5-4" to ensure that there is no reverse flow of noxious gases. The invention is designed to provide UV-C light that irradiates most or all of the drain pipe 20 over the height h and, preferably, along the entire height H.

Figure 2:
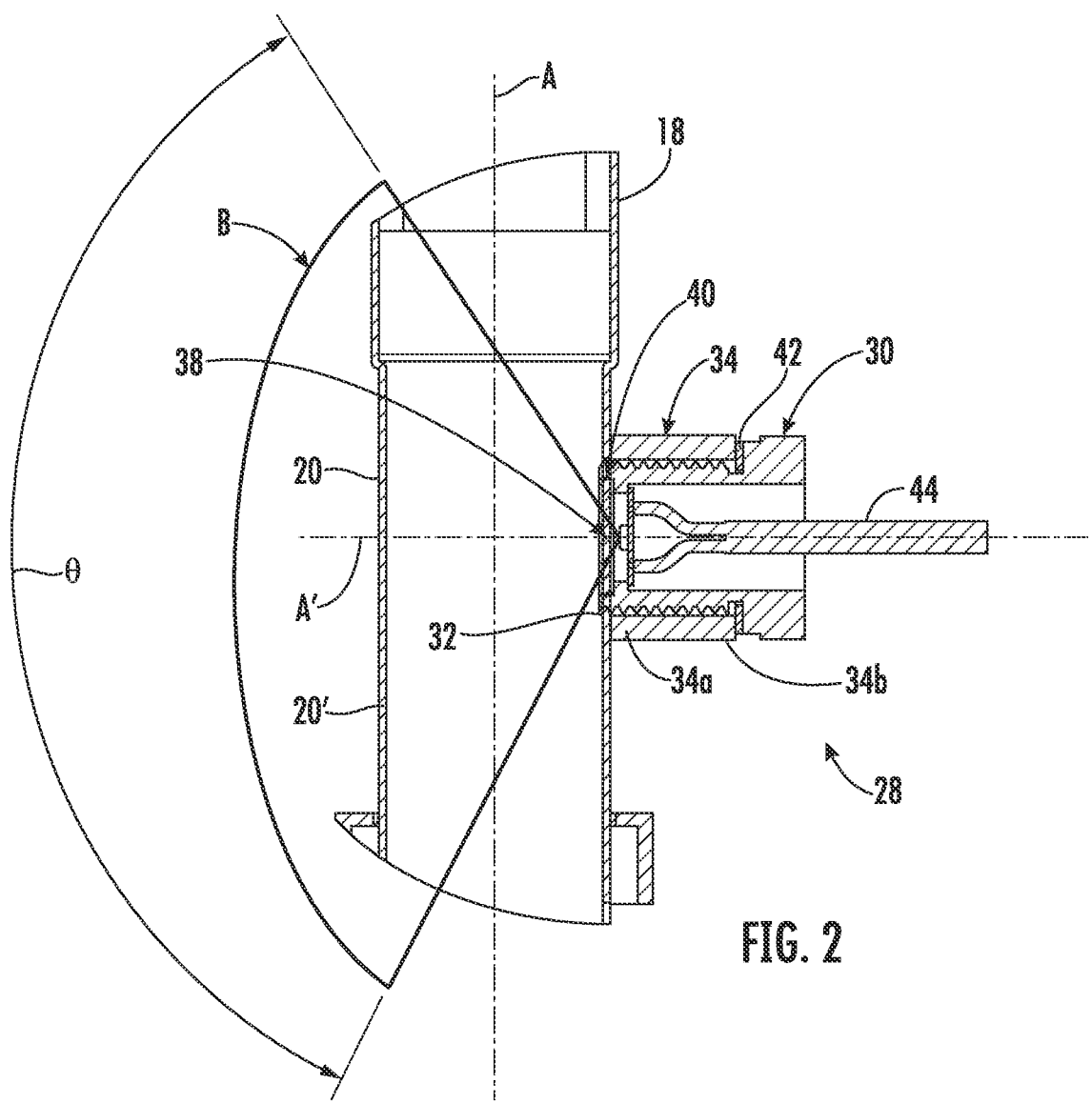
FIG. 2 is an enlarged detail, in cross-section, showing the manner in which the drain disinfecting device interfaces with the drain pipe shown in FIG. 1, showing how a UV-C LED module is secured to the drain pipe.

In FIG. 1 a drain disinfecting device in accordance with the invention is generally designated by the reference numeral 28. The device 28 includes at least one UV-C LED module 30 (FIG. 2). The drain pipe 20 is typically a conventional cylindrical tube or pipe that has a tubular wall 20' defining an interior space and interior surface, and it is formed with a hole, opening or aperture 32 between the tail piece 18 and the trap 24a above the overflow level 26 and can be close or proximate to the tail piece 18 although the precise position is not critical. The module 30 is positioned and oriented to be aligned with or register with the hole 32 along an axis A' that is normal to the axis A of the drain pipe.

Figure 3:
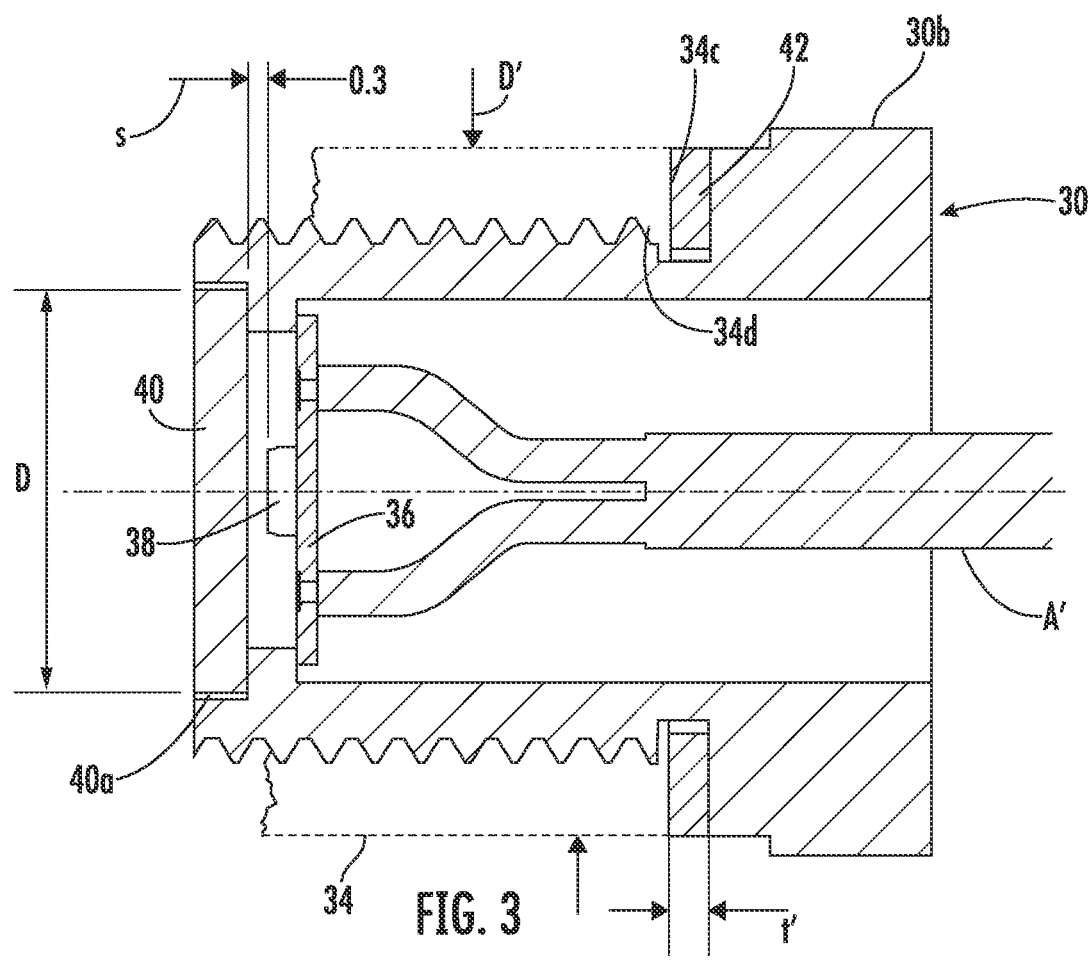
FIG. 3 is an enlarged view of the UV-C LED module shown in FIG. 2.

In a presently preferred embodiment a cylindrical sleeve 34 is aligned with the hole 32 along the axis A' and has one axial end 34a integrally formed with or fixedly joined to the drain pipe 20 and has an opposing free axial end 34b that defines a first annular bearing surface 34c (FIG. 3). The sleeve 34 is provided with an internal thread 34d.

The LED module 30 is provided with a externally threaded cylindrical end 30a configured to be received within the internally threaded end 34b of the sleeve 34 to threadedly mesh with the sleeve and move along the axis A' relative to the fix or stationary sleeve along the axis A' with rotation of the module 30 relative to the fixed sleeve 34. A printed circuit board 36 is provided within the module 30 for mounting a UV-C LED 38. A quartz or other UV-C transparent lens 40 is provided, the lens 40 forming a transparent medium through which UV light can be transmitted with minimal or no attenuation.

The UV-C LED 38 when energized generates a radiation beam B having a predetermined radiation angle θ to transmit UV-C light into the drain pipe section 20 through the hole 32 to irradiate at least a portion of the interior surface and also expose airborne pathogens contained within the air column above the level 26 to UV-C light in proximity to the drain inlet at the tail piece 18.

The lens 40 is positioned generally coextensively with the tubular wall 20'. The lens 40 in the embodiment shown is a flat circular lens having a peripheral or circumferential edge 40a generally coextensive with the hole 32. Lenses other than flat lenses, such as convex or concave lenses, may be used to converge or diverge the beam B to effectively decrease or increase the angle θ, with different degrees of advantage.

Figure 4:
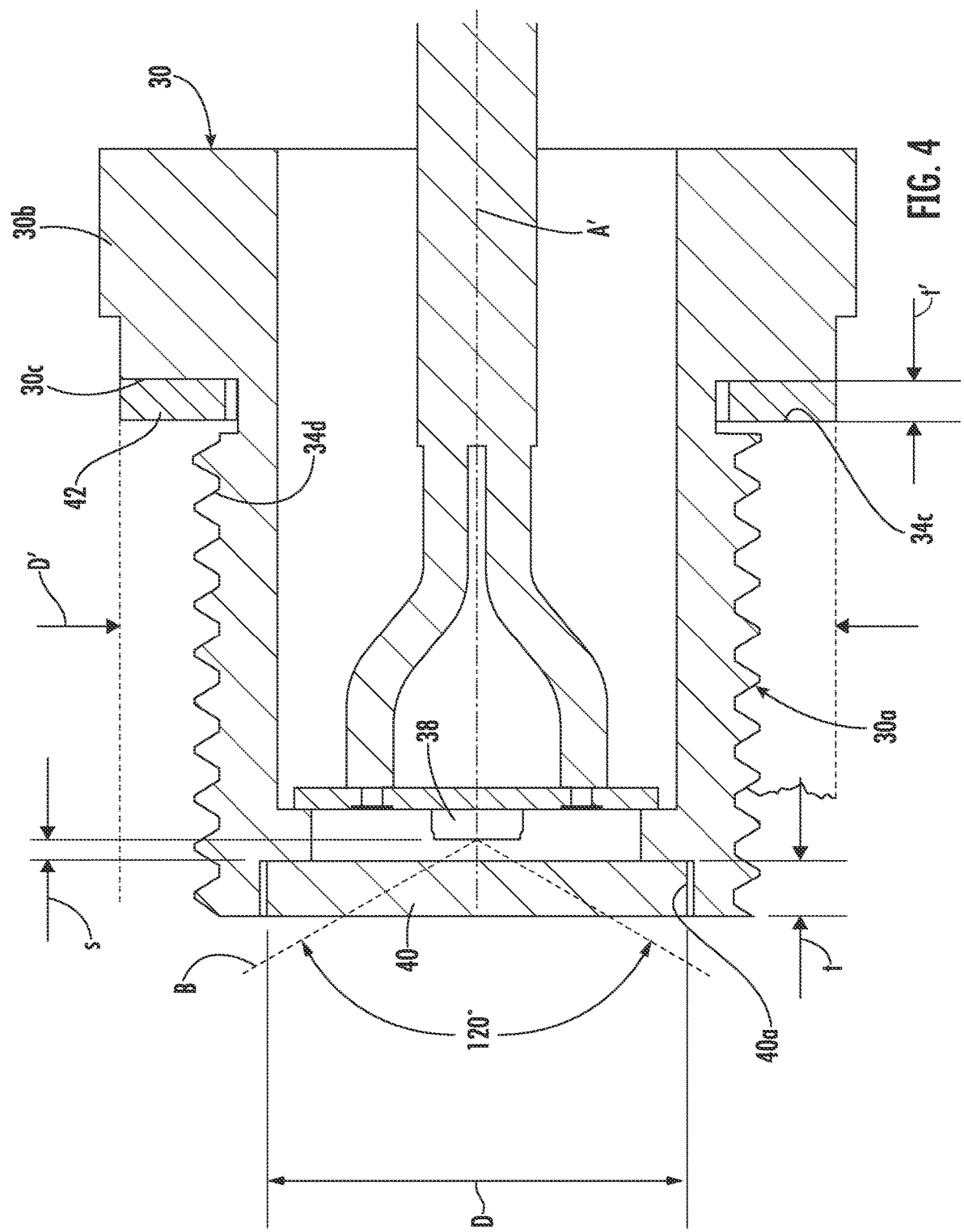
FIG. 4 is similar to FIG. 3, showing a radiation beam emanating from a UV-C LED spaced a distance less than an optimal distance in accordance with the invention.
Figure 5:
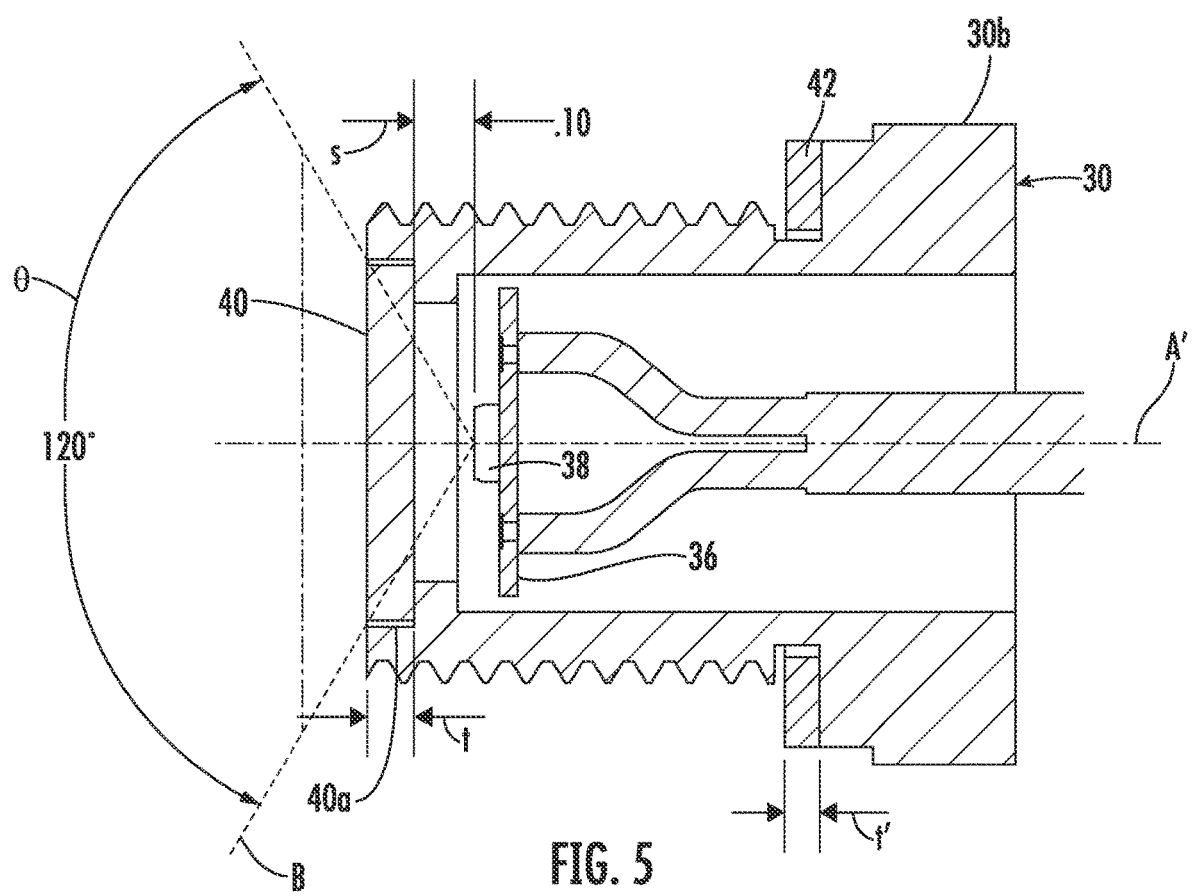
FIG. 5 is similar to FIG. 4, showing the UV-C LED spaced at a distance from the lens that maximizes exposure of the interior of the drain pipe to UV-C light in accordance to the invention.

An important feature of the invention is the selection of the spacing "s" between the UV-C LED 38 and the lens 40 to maximize the degree of exposure of the interior surface of the drain pipe to the UV-C light beam B. Referring to FIG. 3 the distance "s" of the UV-C LED 38 from the lens 40 is critical. When "s" is less than a critical value, referring to FIG. 4, the beam B does not reach the peripheral edge 40a and the beam B covers less of the internal surface area of the drain pipe. As the distance "s" is increased, referring to FIG. 5, the radiation pattern on the interior surface increases with the optimum value of "s" being selected when the beam B passes through the outer region of the lens 40 and optimally through the peripheral edge 40a. Increasing the distance "s" beyond the preferred value causes the beam to be blocked or cut off by the supporting structure of the module 30, again reducing the effective coverage of the interior surface. When a flat lens 40 is spaced from the UV-C LED a distance "s" and has a thickness "t", the radiation angle is "θ" and the lens has a diameter "D" the optimum distance s=D/[2 tan (θ/2)]−t. While s in the optimum spacing for best performance, with slight deviations within a critical range still provide good results with slightly different degrees of performance. A critical range for the spacing s is $s_c$=s±0.1 s without significant deterioration or effectiveness. In one example, the UV-C LED generates a radiation beam having a radiation angle of 120°, the lens 40 has a diameter of 0.625 inches and a thickness of 0.08 inches so the optimum spacing "s" is 0.1 inches from the lens. While the specific LED has a radiation pattern of 120°, there are different factors that affect the radiation pattern of an LED. One of these factors is the lens type of the LED. When the LED has a flat window lens this results in a wider angle of emission when compared to a curved lens. Another factor is whether the LED is a surface emitter or a volume emitter. Surface emitters have a maximum emission angle of 90°.

Another feature of the invention is that the UV-C LED module is removably attachable to the tubular wall 20' for replacement or maintenance. Referring to FIGS. 2-5 this is achieved by providing a threaded sleeve 34 fixedly secured to the drain pipe section 20 and providing a UV-C LED module 30 that is formed with a threaded member or portion 30a threadedly engageable with the threaded sleeve 34 and configured to position the UV-C LED 38 at a predetermined optimum distance "s" when the sleeve 34 and the member or module 30 are fully threadedly engaged as shown in FIG. 2. A shown, the sleeve is internally threaded and member or module is externally threaded.

In the depicted embodiment the sleeve 34 is a circular cylinder having one axial end 34a fixed to the drain pipe section 20 and has an opposing axial free end 34b formed with a first annular bearing surface 34c and the member or module 30 is formed with an enlarged collar 30b forming a second annular bearing surface 30c, 34c. The first and second bearing surfaces are like annular surfaces that have the same or substantially equal outer diameter D' that face each other. An annular washer 42 also having an outer diameter substantially equal to D' is interposed between the first and second annular surfaces 30c, 34c to provide a compression contact between the washer and the first and second annular surfaces when the sleeve 34 and member or module 30 are fully threadedly engaged in the operative condition as shown in FIG. 2. The washer 42 has a thickness "t'" selected to provide both a seal between the sleeve 34 and the module 30 and to position the UV-C LED at the predetermined or optimum desired distance from the lens within the critical range when the first and second annular surfaces 30c and 34c abut against the washer when the sleeve and the module are fully threadedly engaged.

While the lens 40 is preferably made of quartz, any suitable glass or transparent material may be used that does not attenuate or unduly attenuate the UV-C radiation beam B.

The UV-C LED 38 is connected by means of electrical conductors 44 within a conduit 46 to a suitable voltage converter that serves as a driver for the LED. A driver 48 is connected to a programmable controller 50 that, in turn, is connected to a source of power, such as a 110 volt power outlet at a J-box 52. The programmable controller 50 is also advantageously connected to a motion detector 54 that can detect motion in the general facility or area of the sink basin. The programmable controller 50 and the voltage converter or driver 48 are preferably enclosed within a box or housing 56 that can be attached to the wall 12. The enclosure 56 is also advantageously water resistant. To facilitate installation, the conduit 46 is preferably a flexible conduit that can be extended between and connected to the casing enclosure 56 and the drain pipe 20.

In FIGS. 1 and 2 only one module 30 is shown. It will be appreciated that two or more modules may also be installed on a single drain pipe. When two or more UV-C LED modules are used they are preferably linearly and angularly spaced or offset from each other in relation to the axis A or length direction of the tail pipe 20 to maximize the surface area exposed to the UVC radiation.

In FIGS. 2 and 3, the lenses 40 are generally flat and abut against the outside surface of the drain pipe to prevent interference with the normal flow of waste water down the drain. However, a greater drain pipe inner surface area exposed to radiation may be obtained by utilizing a spherical or conical surface lens that projects only slightly into the interior of the drain pipe. This allows the UV-C LED to be moved closer to the center of the drain pipe. However, such extension of the module into the drain pipe should normally not exceed ¼ of an inch to insure the normal flow and operation of the drain pipe.

The depth at which the device is inserted into the wall of the drainpipe must also be considered. The design is meant to insert the device 0.02 inches or a negligible distance into the pipe as seen on the drawing. The device is preferably inserted a very small distance into the pipe to ensure the radiation pattern is not interfered. This distance is very small so essentially the system is along the wall of the pipe and does not interfere with water flow in the drain pipe.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A disinfecting device for disinfecting the interior of a drain pipe leading from a drain inlet of a sink basin to a U-shaped trap beneath the sink basin, the device comprising a drain pipe section below or downstream of the sink drain inlet, said drain pipe section having a cylindrical tubular wall having a substantially circular cross-section and having a predetermined thickness and defining an interior space and interior surface and formed with a hole in said tubular wall between the sink drain inlet and the U-shaped trap; at least one UV-C LED module positioned to register with said hole and including a UV-C LED that when energized generates a radiation beam having a predetermined radiation angle "θ" to transmit UV-C light into said drain pipe section through said hole to irradiate at least a portion of said interior surface and pathogens contained therein with UV-C light in proximity to said drain inlet; a substantially flat transparent lens having a diameter "D" and at least partially coextensive with said tubular wall thickness and arranged within said hole, said lens having an inwardly facing surface substantially tangent to a point on said interior surface of said tubular wall aligned with said hole; and energizing means for energizing said at least one UV-C LED module, said UV-C LED being spaced a distance from said lens a predetermined distance "s" and a thickness "t" to cause said radiation beam to irradiate said inner surface along at least a portion of said drain pipe proximate to said lens, wherein $$s = D/[2\tan(\theta/2)] - t,$$

whereby energizing said at least one UV-C LED module maximizes exposure of pathogens on said interior surface and airborne pathogens within said interior space to said UV-C conical radiation beam and reduces the ability of pathogens from entry into the sink basin.

2. A drain disinfecting device as defined in claim 1, wherein said UV-C LED module is removably attachable to said drain pipe section.

3. A drain disinfecting device as defined in claim 2, wherein a threaded sleeve is fixedly secured to said drain pipe section and wherein said UV-C LED module comprises a threaded member threadedly engageable with said threaded sleeve and configured to position said UV-C LED at said predetermined distance when said sleeve and said member are fully threadedly engaged.

4. A drain disinfecting device as defined in claim 3, wherein said sleeve is internally threaded and said member is externally threaded.

5. A drain disinfecting device as defined in claim 4, wherein said sleeve is a circular cylinder having one axial end fixed to said drain pipe section and having an opposing axial end formed with a first annular surface and said member being formed with a second annular surface; and further comprising an annular washer interposed between said first and second annular surfaces.

6. A drain disinfecting device as defined in claim 5, wherein said washer has a thickness selected to provide a seal between said sleeve and said member and to position said UV-C LED at said predetermined distance from said lens when said first and second annular surfaces abut against said washer when said sleeve and said member are fully threadedly engaged.

7. A drain disinfecting device as defined in claim 1, wherein said UV-C LED generates a radiation beam having a radiation angle θ of 120°, said lens having a diameter of D equal to 0.625 inches and a thickness t of 0.08 inches and said UV-C LED is spaced 0.1 inches from said lens.

8. A drain disinfecting device as defined in claim 1, wherein said UV-C LED module is removably attachable to said drain pipe section.

9. A drain disinfecting device as defined in claim 7, wherein said distance does not exceed 0.2 inches.

* * * * *